United States Patent [19]
Wang

[11] Patent Number: 5,895,646
[45] Date of Patent: *Apr. 20, 1999

[54] ISOLATED NATIVE PRIMATE GM-CSF PROTEIN

[75] Inventor: Elizabeth A. Wang, Carlisle, Mass.

[73] Assignee: Novartis Corporation, Basel, Switzerland

[*] Notice: This patent is subject to a terminal disclaimer.

[21] Appl. No.: 08/344,809

[22] Filed: Nov. 23, 1994

Related U.S. Application Data

[63] Continuation of application No. 08/183,099, Jan. 14, 1994, abandoned, which is a continuation of application No. 08/023,146, Feb. 24, 1993, abandoned, which is a continuation of application No. 07/752,250, Aug. 28, 1991, abandoned, which is a continuation of application No. 07/657,350, Feb. 15, 1991, abandoned, which is a continuation of application No. 06/652,742, Sep. 19, 1984, abandoned.

[51] Int. Cl.$^6$ ............................ C07K 14/535; C07K 1/26
[52] U.S. Cl. ............................ 424/85.1; 530/351; 530/412; 514/2; 514/8; 514/12; 930/145
[58] Field of Search ........................ 530/350, 351, 530/395, 412; 435/69.5; 930/140, 145; 424/85.1; 514/2, 8, 12

[56] References Cited

U.S. PATENT DOCUMENTS

| | | | |
|---|---|---|---|
| 4,230,697 | 10/1980 | Nishida et al. | 424/177 |
| 4,289,690 | 9/1981 | Pestka et al. | 260/112 |
| 4,438,032 | 3/1984 | Golde et al. | 260/112 |
| 4,621,050 | 11/1986 | Sugimoto | 435/68 |
| 4,658,018 | 4/1987 | Urdal et al. | 530/351 |
| 4,677,195 | 6/1987 | Hewick et al. | 530/397 |

FOREIGN PATENT DOCUMENTS

| | | |
|---|---|---|
| 0183350 | 6/1986 | European Pat. Off. . |
| 2058081 | 4/1981 | United Kingdom . |
| 8504188 | 9/1985 | WIPO . |
| 8603225 | 6/1986 | WIPO . |

OTHER PUBLICATIONS

Yunis, et al., FEBS Letters, 1978, 90: 279–82.
Wu, et al. J. Biol. Chem., 1979, 254: 6226–28.
Gasson, et al. Science, 1984, 226: 1339–1342.
Fojo, et al., Biochemistry, 1978, 17: 3109–16.
Lusis, et al., Blood, 1981, 57: 13–21.
Nicola, et al., Blood, 1979, 54: 614–27.
Fojo, et al., Biophys. Acts., 1977, 494: 92–99.
Price, et al., Biochem. J., 1975, 148: 209–17.
Metcalf, The Hemopoietic Colony Stimulating Factors, Elsevier (1984), pp. 81–84, 215–227, 309–329.
Nicola et al., "Preparation of Colony Stimulating Factors From Human Placental Conditioned Medium", Leukemia Res. 4:313 (1978).
Nicola et al., "Separation of Functionally Distinct Human Granulocyte–Macrophage Colony–Stimulating Factors", Blood 54:614 (1979).
Ratzan and Tunis, "Colony Stimulating Factor from Human Placenta", Clinical Res. 22:402A (1974).
Burgess et al., "Stimulation by Human Placental Conditioned Medium of Hemopoietic Colony Formation by Human Marrow Cells", Blood 49:573 (1977).
Fojo et al., "The Isolation and Characterization of a Colony Stimulating Factor from Human Lung", Biochem. Biophys. Acts 494:92(1977).
Yunis et al., "Purification of a Colony Stimulating Factor from Culture Cell Lines Propagated from Human Lung", FEBS Letters 90:279(1978).
Miller et al., "Heterogeneity of Human Colony–Fomring Cells (CFU–C): Differences in Size, Rate of Colony Formation, and Responsiveness to Colony–stimulating Factor", J. Lab. Clin. Med. 92:38 (1978).
Cline and Golde, "Production of Colony–Stimulating Activity by Human Lymphocytes", Nature 248:703 (1974).
Lusis and Koeffler, "Action of Granulocyte–Macrophage Colony–Stimulating Factors: Studies Using a Human Leukemia Cell Line", Proc. Natl. Acad. Sci. USA 77:5346 (1980).
Shah et al., "Characterization of Colony–stimulating Activity Produced by Human Monocytes and Phytohemagglutinin–stimulated Lymphocytes", Blood 50:811 (1977).
Inoue and Ottenbreit, "Heterogeneity of Human Colony–forming Cells", Blood 51:195 (1978).
Wu, "Properties and Separation of T Lymphocyte Growth Stimulatory Activity (TL–GSA) and of Granulocyte–Macrophage Colony Stimulatory Activity (GM–CSA) Produced Separately from Two Human TLymphocyte Subpopulations", J. Cell. Physiol. 101:237 (1979).
Parker and Metcalf, "Production of Colony–stimulating Factor in Mixed Leucocyte Cultures", Immunology 26:1039 (1974).
Iscove et al., "Colony Formation by Normal and Leukemic Human Marrow Cells in Culture: Effect of Conditioned Medium From Human Leukocytes", Blood 37:1 (1971).
Price et al., "The Isolation and Properties of Granulocytic Colony–Stimulating Activities fro Medium Conditioned by Human Peripheral Leukocytes", Biochem. J. 148:209 (1975).

(List continued on next page.)

*Primary Examiner*—Prema Mertz
*Attorney, Agent, or Firm*—Fitzpatrick, Cella, Harper & Scinto

[57] ABSTRACT

A method for purifying CSF protein is described. The method comprises: precipitating the protein with ammonium sulfate at 80% saturation to form a pellet containing the CSF protein; resuspending the pellet in a buffered solution at a pH in the range of about 6 to about 8; applying the buffered solution containing CSF to a chromatographic column, eluting with the buffered solution containing sodium chloride and collecting the fractions having CSF activity; pooling the active fractions, applying them to a C4 reverse phase column and eluting with a 0 to 90% acetonitrile gradient to collect the active fractions. The purified CSF protein has a specific activity of at least about $1\times10^7$ units per mg of protein and preferably at least about $4\times10^7$ units per mg of protein when assayed using the human bone marrow assay.

10 Claims, 2 Drawing Sheets

OTHER PUBLICATIONS

Chervenik and LoBuglio, "Human Blood Monocytes: Stimulators of Granulocyte and Mononuclear Colony Formation in vitro", Science 178:164 (1972).

Moore et al., "Monocyte Production of Colony Stimulating Factor in Familial Cyclic Neutropenia", *British Journal of Haematology* 27:47 (1974).

Okabe et al., "Establishment and Characterization of a Human Cancer Cell Line that Produces Human Colony–stimulating Factor", Cancer Res. 38:3910 (1978).

DiPersio et al., "Human Cell Lines that Elaborate Colony–stimulating Activity for the Marrow Cells of Man and Other Species", Blood 51:507 (1978).

Di Persio et al., "The Fractionation, Characterization and Subcellular Localization of Colony–Stimulating Activities Released by the Human Monocyte–Like Cell Line GCT", Blood 56:717 (1980).

Abboud et al., "Hydrophobic Adsorption Chromatography of Colony–Stimulating Activities and Erythroid–Enhancing Activity From the Human Monocyte–Like Cell Line, GCT", Blood 58:1148 (1981).

Wu, M.–C., et al., "Purification of a Colony Stimulating Factor from Cultured Pancreatic Carcinoma Cells", J. Biol. Chem. 254:6226 (1979).

Wu,. M.–C., and Yunis, "Common Pattern of Two Distinct Types of Colony Stimulating Factor in Human Tissues and Cultured Cells", J. Clin. Invest. 65:772 (1980).

Walasek et al., "Separation of Human and Murine Granulocyte Colony Stimulating Activity", Fed. Proc. 35:1627 (1976).

Suda et al., "A Case of Lung Cancer Associated with Granulocytosis and Production of Colony–Stimulating Activity by the Tumor," Br. J. Cancer 41:980 (1980).

Asano et al., "Demonstration of Granulopoetic Factor(s) in the Plasma of Nude Mice Transplanted with a Human Long Cancer and in the Tumor Tissue", Blood 49:845 (1977).

Sato et al., "Granulocytosis and Colony–Stimulating Activity (CSA) produced by a Human Squamous Cell Carcinoma", Cancer 43:605 (1979).

Asano et al., "Detection and Assessment of Human Tumors Producing Granulocyte–Macrophage Colony–Stimulating Factor (GM–CSF) by Heterotransplantation into Nude Mice", Br. J. Cancer 41:689 (1980).

Lusis et al., Translation of mRNA for Human GM–CSF, Nature 298 (No. 1), 75–77 (1982).

Metcalf, "Production of Colony Stimulating Factors by Lymphoid Tissues," in Biology of the Lymphokines, pp. 515–540 (Academic Press, New York, 1979).

Metcalf et al., Biologic Properties in Vitro of a Recombinant Human Granulocyte–Macrophage Colony Stimulating Factor, Blood 67:37 (1986).

Metcalf, "The Molecular Biology and Functions of the Granulocyte–Macrophage Colony Stimulating Factors", Blood 67:257 (1986).

Tomonaga et al., "Biosynthetic (Recombinant) Human Granulocyte–Macrophage Colony-Stimulating Factor: Effect on Normal Bone Marrow and Leukemia Cell Lines", Blood 67:31 (1986).

Gasson et al., Purification Human Granulocyte–Macrophage Colony–Stimulating Factor; Direct Action on Neutrophils, Science 226, Dec. 14, 1984.

Westbrook et al., Purification and Characterization of Human T–lyphocyte–derived Erythroid–potentiating Activity, J. Biol. Chem. vol. 259, No. 16, 9992–6, Aug. 25, 1984.

Nicola et al., Binding of the Differentiation–inducer, GM–CSF, to responsive but not unresponsive leukemic cell lines, Proc. Natl. Acad. Sci. 81 3765–3769, Jun. 1984.

Fojo et al., Purification and Chaaracterization of a Colony Stimulating Factor from Human Lung, Biochemistry 17, No. 15 (1978).

Lusis et al., Blood 57, 13–21 (1981).

Gough et al., Nature 309, 763–767 (1984).

Fung et al., Nature 307, 233–236 (1984).

```
                10                        30                            45
GAATTCCGCT  GGAGG ATG TGG CTG CAG AGC CTG CTG CTC TTG GGC ACT GTG GCC TGC
                  MET Trp Leu Gln Ser Leu Leu Leu Leu Gly Thr Val Ala Cys 60                  75                    90                      105
AGC ATC TCT GCA CCC GCC CGC TCG CCC AGC CCC AGC ACG CAG CCC TGG GAG CAT
Ser Ile Ser Ala Pro Ala Arg Ser Pro Ser Pro Ser Thr Gln Pro Trp Glu His 120                    135                    150                165
GTG AAT GCC ATC CAG GAG GCC CGG CGT CTC CTG AAC CTG AGT AGA GAC ACT GCT
Val Asn Ala Ile Gln Glu Ala Arg Arg Leu Leu Asn Leu Ser Arg Asp Thr Ala 180                       195                   210
GCT GAG ATG AAT GAA ACA GTA GAA GTC ATC TCA GAA ATG TTT GAC CTC CAG GAG
Ala Glu MET Asn Glu Thr Val Glu Val Ile Ser Glu MET Phe Asp Leu Gln Glu 225                    240                   255                    270
CCG TCC TGC CTA CAG ACC CGC CTG GAG CTG TAC AAG CAG GGC CTG CGG GGC AGC
Pro Ser Cys Leu Gln Thr Arg Leu Glu Leu Tyr Lys Gln Gly Leu Arg Gly Ser 285                     300                   315
CTC ACC AAG CTC AAG GGC CCC TTG ACC ATG ATG GCC AGC CAC TAC AAG CAG CAC
Leu Thr Lys Leu Lys Gly Pro Leu Thr MET MET Ala Ser His Tyr Lys Gln His 330                    345                    360                    375
TGC CCT CCA ACC CCG GAA ACT TCC TGT GCA ACC CAG ACT ATC ACC TTT GAA AGT
Cys Pro Pro Thr Pro Glu Thr Ser Cys Ala Thr Gln Thr Ile Thr Phe Glu Ser 390                    405                       420                    435
TTC AAA GAG AAC CTG AAG GAC TTT TTG CTT GTC ATC CCC TTT GAC TGC TGG GAG
Phe Lys Glu Asn Leu Lys Asp Phe Leu Leu Val Ile Pro Phe Asp Cys Trp Glu 450          460          470         480          490         500
CCA GTC CAG GAG     TGA GACCGGCCAG ATGAGGCTGG CCAAGCCGGG GAGCTGCTCT CTCATGAAAC
Pro Val Gln Glu 510         520         530         540         550         560         570
AAGAGCTAGA AACTCAGGAT GGTCATCTTG GAGGGACCAA GGGGTGGGCC ACAGCATGGT GGGAGTGGCC 580         590         600         610         620         630         640
TGGACCTGCC CTGGGCCACA CTGACCCTGA TACAGGCATG GCAGAAGAAT GGGAATATTT TATACTGACA 650         660         670         680         690         700         710
GAAATCAGTA ATATTTATAT ATTTATATTT TTAAAATATT TATTTATTTA TTTATTTAAG TTCATATTCC 720         730         740         750         760         770         780
ATATTTATTC AAGATGTTTT ACCGTAATAA TTATTATTAA AAATATGCTT CTAAAAAAAA AAAAAAAAA
```

FIG. 1

ISOLATED NATIVE PRIMATE GM-CSF PROTEIN

This is a continuation of application Ser. No. 08/183,099, filed Jan. 14, 1994, now abandoned, which in turn is a continuation of application Ser. No. 08/023,146, filed Feb. 24, 1993, now abandoned, which in turn is a continuation of application Ser. No. 07/752,250, filed Aug. 28, 1991, now abandoned, which in turn is a continuation of application Ser. No. 07/657,350, filed Feb. 15, 1991, now abandoned, which in turn is a continuation of application Ser. No. 06/652,742, filed Sep. 19, 1984, now abandoned.

FIELD OF THE INVENTION

This invention relates to the purification of a protein having the ability to stimulate the growth and differentiation of primate hematopoietic progenitor cells, i.e. colony stimulating factor (CSF) protein, particularly a method for purifying CSF protein and substantially pure CSF protein obtained thereby.

BACKGROUND OF THE INVENTION

The many different cell types found in blood are all derived from pluripotent hematopoietic stem cells. Stem cells perform two functions: (1) they reproduce themselves, thereby maintaining a stem cell population in the body and (2) they provide progeny cells committed to differentiate into any of the mature blood cell types. The cell which is committed to differentiate along a particular hematopoietic pathway is termed a progenitor cell. Progenitor cells for T lymphocytes, B lymphocytes, granulocytes, macrophages, red blood cells, platelets, and eosinophils, as well as earlier progenitors which can individually give rise to several of the mature cell types, have been studied experimentally both in vivo and in vitro (Dexter, T. M. 1983 J. Pathology 141 415–433). It has been determined in vitro that proliferation and/or differentiation of each progenitor cell type depends upon specific "factors" which have been obtained from various sources. For example, the later progenitors of red blood cells require for their proliferation and differentiation a factor called erythropoietin. The factors required for survival, proliferation and differentiation of the progenitor cells committed to form mature neutrophilic granulocytes and macrophages are called colony stimulating factors (CSFs).

CSF activity has been studied extensively in the mouse. Most adult mouse organs produce CSF activity. However, compositions containing CSF activity that have been obtained from various tissues and by various methods appear to differ in their biochemical characteristics. Thus, the structural relationships between the different factors remain unknown. Furthermore, CSF activity appears to act at more than one step of granulocyte and macrophage development, and again it has been uncertain whether a single factor is responsible for all of the observed activities or whether a different factor acts at each step (Burgess, A. and Metcalf, D. 1980 Blood 56 947–957).

Human CSF activity has been obtained from placenta, certain fetal tissues, macrophages, and stimulated T cells. A line of T cells (Mo) that produces one or more potent CSF activities was established from a patient with a T cell variant of hairy cell leukaemia (leukaemic reticuloendotheliosis) (Golde et al 1978 Blood 52 1068–1072).

The ability of CSF activity to stimulate granulocyte and macrophage production indicates that pharmaceutical compositions having CSF activity are clinically useful in situations where increased production of these (myeloid) cell types is required. Indeed, several patients with extremely high levels of apparently normal circulating granulocytes have been shown to have tumors which over-produce CSFs. In one case, upon surgical removal of the tumor, the granulocyte count rapidly declined towards a normal level, strongly suggesting that CSFs may be useful in regulating the numbers of circulating granulocytes. (Hocking, W., Goodman, J., and Golde, D. Blood 61 600 (1983)). In particular, CSF compositions are useful clinically for the treatment of myelo-suppression caused by chemotherapeutical or irradiation treatment of cancer. In addition, CSF compositions are useful in treating severe infections because CSF can increase and/or activate the number of granulocytes and/or monocytes.

Biological and biochemical characterization of compositions having CSF activity, and study of these compositions in the clinical setting have been hampered to date by the scarcity and impurity of human and/or other primate CSF compositions. It can be appreciated that it would be desirable to identify the protein or proteins responsible for CSF activity. Furthermore, it would be desirable to have a primate, preferably human, source of such CSF activity that could readily supply these proteins in quantities and purity sufficient for biological and biochemical characterization and for use as therapeutic agents.

The Mo cell line has been used both as a starting material for purifying human CSFs and for identifying the corresponding messenger RNAs. However, even with this relatively good source of CSF activity, it has proved to be extremely difficult to isolate protein having sufficient purity for structural studies. Thus, new and better methods for purifying CSFs are desired.

SUMMARY OF THE INVENTION

The present invention overcomes the problems of the prior art and provides a method for purifying protein having CSF activity. CSF protein in accord with the present invention, has a specific activity of at least about $1 \times 10^7$ units per mg of protein and preferably at least about $4 \times 10^7$ units per mg of protein when assayed using the human bone marrow assay.

In accord with the present invention, a method for purifying CSF protein comprises: precipitating the protein with ammonium sulfate at 80% saturation to form a pellet containing the CSF protein; resuspending the pellet in a buffered solution at a pH in the range of about 6 to about 8; applying the buffered solution containing CSF to a chromatographic column, eluting with the buffered solution containing sodium chloride and collecting the fractions having CSF activity; pooling the active fractions, applying them to a C4 reverse phase column and eluting with a 0 to 90% acetonitrile gradient to collect the active fractions.

The CSF proteins of this invention are growth and differentiation hormones for the cells of the myeloid system. They are useful clinically for the treatment of myelo-suppression especially (sympotomatic) granulocyto-penia following chemotherapeutical or irradiation treatment of cancer.

BRIEF DESCRIPTION OF THE DRAWINGS

FIG. 1 illustrates the DNA sequence that codes for a CSF protein. The Arrow in FIG. 1 shows the beginning of the mature 127 amino acid residue peptide sequence comprising a GM-CSF protein as coded for by such DNA sequence.

DETAILED DESCRIPTION OF THE INVENTION

Figure 2:
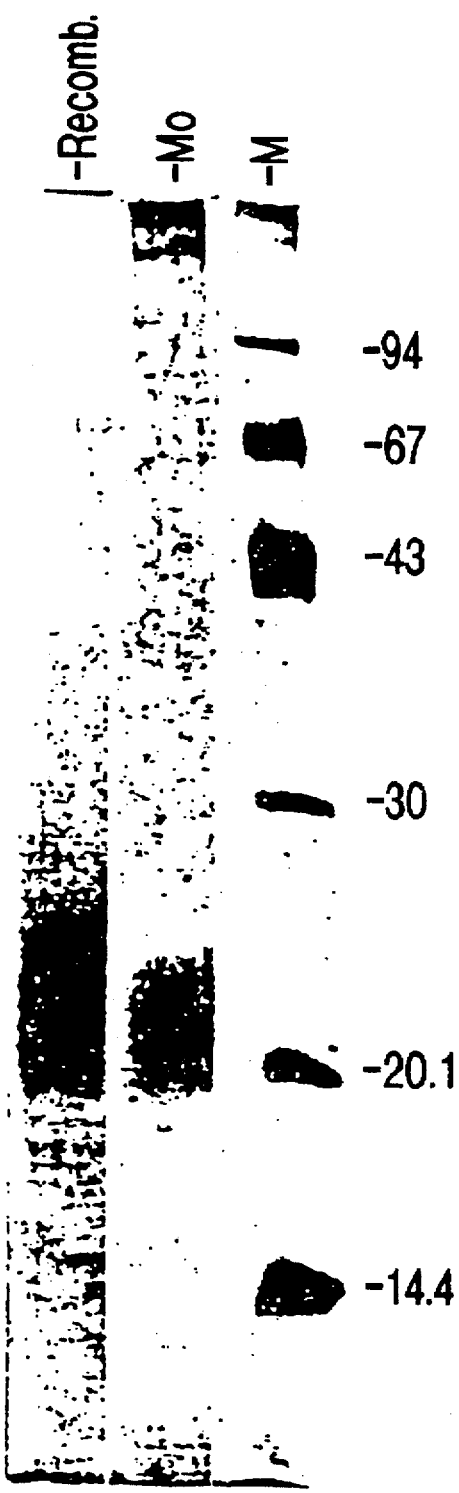
FIG. 2 illustrates SDS-PAGE analysis of the purified CSF protein.

Colony-stimulating factor activity (CSF) can be derived from a number of cellular sources including conditioned medium from peripheral blood mononuclear cells, lung and placental tissue, and bone marrow, urine from anemic patients, serum, and normal and neoplastic cells of T-lymphocyte and mononuclear phagocyte lineage. One cell line that produces CSF is the Mo cell line. The CSF produced by this cell line is known as granulocyte-macrophage CSF (or GM-CSF).

CSFs can also be produced using recombinant DNA techniques to clone CSF/cDNA and DNA that expresses CSF can be transfected into suitable host cells for expression of CSF protein. See copending and later abandoned application U.S. Ser. No. 628,342 filed Jul. 6, 1984, which is hereby incorporated by reference.

CSFs from any source can be purified by the process of the present invention. The conditioned medium from any source of CSF protein is preferably concentrated by ultra-filtration to a protein concentration of at least about 0.1 mg protein per ml. The protein is then precipitated by adding ammonium sulfate to 80% of saturation. The resulting pellet is resuspended in an aqueous solution buffered at a pH in the range of about 6 to about 8. Examples of suitable buffers include Tris-HCl, HEPES, sodium citrate, and the like.

The buffered solution is fractionated by column chromatography. Suitable materials for use in the chromatography column are octylsepharose, DEAE-ultrogel, AcA44-ultrogel, and the like. One or more of these materials can be used in sequence to obtain higher purity.

Fractions from each column are collected and assayed for CSF activity. The active fractions are pooled and diluted with trifluoroacetic acid (TFA), heptafluorobutyric acid (HFBA), or the like, and applied to a C4 reverse phase column. The CSF activity is then eluted using a 0–90% acetonitrile gradient in TFA or HFBA, preferably at a concentration of 0.10% or 0.15% (vol/vol) respectively, depending upon which acid was used to apply the pooled fractions to the column.

The fractions having CSF activity are analyzed by SDS polyacrylamide gel electrophoresis (13.5% gel as described by Lammli, U. Nature 227, 680 (1970)). Additional treatments using the above mentioned chromatographic column materials can further purify the CSF protein to homogeneity.

Purified CSF protein fractionated by SDS-PAGE revealed a heterogeneous CSF protein having an apparent molecular weight in the range of about 15,000 to about 26,000 daltons. This apparent size heterogeneity is due to the extensive glycosylation of the protein and is a common feature of glycoproteins. Fractionation of less purified samples from Mo cell conditioned medium by SDS-PAGE (under non-reducing conditions) and assaying protein eluted from the gel revealed the presence of a second protein having CSF activity having an apparent molecular weight of about 28,000 to 30,000.

CSF activity binds and elutes from octylsepharose, DEAE ultrogel and the C4 reverse phase column. Roughly 60% of the CSF activity binds a Con-A sepharose (40% flow through) and can be eluted with alpha methylmannoside. Molecular weight analysis of recombinant CSF by gel filtration in low salt revealed that about 30% of the activity eluted with an estimated molecular weight of about 19,000 but 70% of the material behaved as dimers, eluting at a position corresponding to a molecular weight of about 38,000. If 1M NaCl is included in this column, all of the activity elutes in a broad peak at about 19,000 daltons.

The purified CSF is stable for at least 16 hours when incubated at 4° C. (pH 7.4) in 4M guanidine hydrochloride; in 10 mM EDTA; 10 mM 2-mercaptoethanol; and in 30% (v/v) ethanol. The CSF activity also is stable in 0.1% trifluroacetic acid (TFA) (pH 2.0) and 0.1% TFA plus 25% (v/v) acetonitrile.

As aforesaid, the CSF protein in accord with the present invention can be used for treatment of myelo-suppression such as (symptomatic) granulocytopenia. For such use, a daily dosage of about 200 to 1000 ug per patient is typically indicated. The CSF protein is preferably injected into the patient intravenously in a suitable pharmacological carrier. Examples of such carriers include pharmacological saline and human serum albumin in saline.

The invention will be further understood with reference to the following illustrative embodiments, which are purely exemplary, and should not be taken as limitive of the true scope of the present invention, as described in the claims. In the examples, unless otherwise specified, temperatures are in ° C. and percents are generally weight/volume percent. All steps in the purification with the exception of the reverse phase HPLC columns are performed at 0–4° C. The reverse phase HPLC is performed at room temperature.

EXAMPLE A

Step 1. Mo Cell Line Cultures

Mo cells (ATCC CRL 8066) were grown routinely in Alpha (6% $CO_2$) or Iscove's (10% $CO_2$) medium containing 20% Fetal Calf Serum (FCS), 2 mM glutamine, 100 U/ml streptomycin and 100 ug/ml penicillin. The cells should be subcultured every 4–5 days. Cells are counted and seeded into Falcon T-175 flasks in 100–150 ml medium at density of 3–4×$10^5$ cells/ml. Cells will double in 20% FCS every 4–7 days. Growth rate is not constant and cells may sometimes appear to stop growing then go through bursts of growth. Mo cells can be grown in serum-free medium. Survival is much better when cells are not washed when transferred from FCS to serum-free medium. Optimal density in Serum-Free medium (SF) in 5×$10^5$ cells/ml. Cells will grow slightly (or at least maintain constant number) for 3 days in serum-free medium, and then should be fed 20% FCS for at least 4 days. This growth schedule (3 days SF, 4 days 20% FCS) can be repeated weekly if SF medium is required, with no apparent harm to the cells for several months.

Step 2. Assays for CSF Activity

A. Bone Marrow Assay

Obtain fresh bone marrow. Break apart spicules by drawing through 20, 22, then 25 gauge needle. Dilute 1:1 with sterile phosphate-buffered saline (PBS) (room temperature) and layer over Ficoll-Paque (about 30 ml BM-PBS over 6 ml Ficoll). Centrifuge at 1500 rpm for 40 minutes at room temperature. Remove fat and PBS layer and discard. Pipette off the light density layer. Wash twice (2×) with PBS and count. Plate cells in RPMI (purchased from GIBCO as RPMI 1640) plus 10% heat inactivated FCS (HIFCS) for 3 hours to remove adherent cells.

Plating medium (make fresh):

20% FCS 0.3% agar dissolved in $H_2O$ cooled to 40° C.

2× Iscoves (1:1 v/v with Agar)

Final concentration of 100 U/ml penicillin, 100 ug/ml streptomycin $10^{-4}$ M alpha thioglycerol in 2× Iscoves from $10^{-2}$ M stock Cool agar to about 40°. Mix with other ingredients.

Cool in $H_2O$ bath to 37–38° and hold at that temperature. After 3 hours, pipette off the non-adherent cells. Spin and count. Add $2 \times 10^5$ cells/ml of plating medium and keep in controlled temperature water bath at 37–38°. Add samples (e.g., medium from transfected cells; usually 10 ul sample) to the first row of wells of a microtiter plate in duplicate. If the sample is not sterile, it should be filtered. This is readily done by adding bovine serum albumin to a final concentration of 0.1 mg/ml then centrifuging the sample through nitrocellulose filters having 0.2 micron pore size using the Schleicher and Schuell microfiltration centrifuge tubes. Add 100 ul cell suspension to each well. Add additional 50 ul of cell suspension to each well in the first row. Mix thoroughly and transfer 50 ul of solution from the first row into the next row, etc. and continue 1:3 dilutions across plate. Wrap the plate in parafilm. Incubate 10–14 days at 10% $CO_2$, 37° C. in fully humidified atmosphere and score colonies.

To score the colonies, the total number of colonies that grow in each well is counted. In each assay, several wells are plated without including a sample (blank) to obtain a background colony count. The average number of colonies that grow in the blank wells is subtracted from the number of colonies found in each of the wells containing samples. One unit of CSF is the amount that will stimulate the formation of one colony above the background level per $10^5$ human bone marrow cells (plated at $10^5$ cells per ml) when the CSF concentration is sub-saturating. The sub-saturating concentration is determined by dilution and comparing the number of colonies at various dilutions to find the concentration just below the saturation level.

For this assay, the colonies containing granulocytes, monocytes or both types of cells are counted. The types of cells in the colonies are determined by picking colonies and staining individual cells.

B. KG-1 Cell Assay

KG-1 cells (*Blood*, Vol. 56, No. 3 (1980)) are grown in Iscoves medium+10% FCS passed 2× per week and seeded for each passage at $2 \times 10^5$ cells/ml. The cells are used for assay only between passage 30–35. The assay is the same as for bone marrow as described above, except the KG-1 cells are plated in agar mixture at $4 \times 10^3$ cells/ml.

The number of colonies growing in each well is determined and the background count is subtracted as in the Bone Marrow assay described above. One KG-1 CSF unit/ml is that concentration of CSF that will stimulate half of the maximum number (saturation) of KG-1 colonies to grow. The maximum number is obtained by including a saturating level of CSF in several wells. The KG-1 assay is convenient for routinely measuring CSF activity but the results must be ultimately confirmed using the bone marrow assay and activity results are generally reported from this latter assay system.

Step 3. Purification of CSF from Mo Cell Line

Mo serum free conditioned medium (40 liters) was incubated at 55° C. for 30 minutes to inactivate the HTLV-II virus associated with the cell line. This medium was concentrated by pressurized ultrafiltration using the Pellicon Casette with membrane PTGC (1.5 square feet) which has a 10,000 molecular weight cut-off. The protein was further concentrated by ammonium sulfate precipitation (80% saturation). The final protein pellet (800 mg) was resuspended in 100 ml of 20 mM tris(hydroxymethyl) aminomethane hydrochlroide (Tris-HCl), pH 7.4, and dialyzed against the same buffer (3 times with 4 liter changes each time). The dialyzed protein was applied to a $2.5 \times 10$ cm column of DEAE (diethylaminoethyl)-ultrogel equilibrated in the same buffer. The column was washed with 800 ml of 20 mM Tris-HCl, pH 7.4, then the CSF activity eluted with 800 ml of 20 mM Tris-HCl, pH 7.4, containing 0.12 M NaCl. 10 ml fractions were collected and assayed for CSF. The active fractions (3) were pooled, and concentrated 6 fold (to 5 ml) by pressurized ultrafiltration (Amicon YM5 membrane, 5,000 molecular weight cut-off). The concentrated sample from the DEAE column was applied to a $1.6 \times 100$ cm AcA44 ultrogel (an acrylamide agarose ultrogel having 10 to 130 k Dalton fractionation) column equilibrated in 20 mM N-2-hydroxyethylpiperazine-N-2-ethane sulfonic acid (HEPES), pH 7.4, 50 mM NaCl, and 0.01% polyethylene glycol (PEG-8000). CSF activity eluted from the column with an apparent molecular weight of 30 k Daltons. The active fractions were pooled and brought to 0.15% (v/v) trifluoroacetic acid (TFA) by addition of 10% TFA and applied to a Vydac $C_4$ reverse phase column ($1 \times 25$ cm). The column was developed with a linear gradient of 0–90% acetonitrile in 0.1% TFA (v/v) at 4 ml/min (1,000 ml total). The CSF activity eluted at approximately 47% (v/v) acetonitrile. The pooled active fractions were brought to 0.05% (v/v) heptafluorobutyric acid (HFBA) by addition of one half volume of 0.15% (v/v) HFBA and applied to a Vydac C4 column ($0.46 \times 25$ cm) equilibrated in 0.15% (v/v) HFBA. The column was developed with a linear gradient of 0–90% (v/v) acetonitrile in 0.15% (v/v) HFBA at 1 ml/min. (340 ml total). The CSF activity eluted at about 53% (v/v) acetonitrile. Fractions 37–44 (1 ml each) were found to be active. 0.15 ml of fraction 40 was concentrated 4 fold (using the SAVANT Speed Vac Concentrator) and 40 ul of 2×SDS gel sample buffer added (0.125 M Tris-HCl, pH 6.8, 4% SDS, 20% glycerol and 0.004% Bromophenol blue). These samples were boiled for 2 minutes and applied to a 13.5% Lammli, U. *Nature* 227, 680 (1970) SDS gel (See FIG. 2). Fraction (#40) was determined to have 110,000 bone marrow CSF units/ml. This corresponds to about $3.0 \times 10^7$ units per $A_{280}$ absorbance unit. Since typical proteins have extinction coefficients ranging between 0.8 and 1.2 $A_{280}$ unit per milligram, the purified CSF had a specific activity in the range of about $1 \times 10^7$ to about $4 \times 10^7$ units per mg in the bone marrow assay. A 1 ug sample of purified GM-CSF was submitted to Edman Degradation using the Applied Biosystems Gas Phase Microsequenator. The sequence of residues 3 through 5 was determined to be Ala Arg Ser.

EXAMPLE B

Step 1. M6 Cos Cell Transfection

M6 COS Monkey cells were grown routinely in Dulbecco's Modified Eagle's Medium (DME available from Gibco) containing 10% heat inactivated (55° for 30 minutes) fetal calf serum (HIFCS). The cells are split 1:6, twice a week. Twenty four hours prior to transfection, $1.2 \times 10^8$ M6 cells (split 1:6) are seeded into a Cell Factory (available from Nunc) in 1.5 liters of DME+10% HIFCS. Immediately before transfection, the medium is aspirated from the cell factory and the cells are washed twice with serum free DME (SF DME).

Plasmid DNA, a cDNA encoding human CSF (as illustrated in FIG. 1) inserted into the eukaryotic expression vector p91023(B) (p91023(B)-CSF) is purified from 2 liters of bacteria by equilibrium density centrifugation in CsCl and ethidium bromide. Details of the construction of vector p91023(B) can be found in copending Ser. No. 628,342. One mg of this DNA was dissolved in 1 ml of 0.1 M Tris, pH 7.3 and added to 600 ml of DME containing 2 mM glutamine, 100 U/ml streptomycin, 100 ug/ml penicillin (P/S) and 0.25 mg/ml DEAE Dextran (Molecular weight 500,000 from Pharmacia). The 600 ml of DNA DEAE Dextran solution is added to the M6 COS cells in the cell factory and incubated at 37° for 12 hours. After the incubation, the cells are rinsed once with 900 ml of SF DME then incubated for 2.5 hours with 600 ml of DME containing 0.1 mM chloroquin, 10% HIFCS, 2 mM glutamine, 100 U/ml penicillin and 100 ug/ml streptomycin. After aspirating the chloroquin containing medium, the cells are rinsed with SF DME and fed 1500 ml of DME with 10% HIFCS. After 30 hours the cells are washed with SF DME, the medium is replaced with 800 ml of SF DME and the transfected cells are allowed to condition the medium for 24 hours at 37° C. The conditioned medium is aspirated and replaced with another 800 ml of SF DME. The cells are allowed to condition this medium for 24 hours then the conditioned medium is collected. As soon as possible after harvesting, the conditioned media sample are concentrated 20 fold by pressurized ultrafiltration using the Amicon 2.5 liter chamber with the YM5 membrane (5,000 MW cutoff).

Step 2. Purification of Recombinant CSF

Two hundred ml of concentrated conditioned medium (from 4 liters of starting material) was brought to 30% saturation of ammonium sulfate by addition of solid ammonium sulfate and the precipitated protein was removed by centrifugation. The supernatant was brought to 80% saturation of ammonium sulfate by adding more solid ammonium sulfate and the precipitated protein collected by centrifugation. The pellet was resuspended in 5 ml of 20 mM sodium citrate, pH 6.1, containing 1 M NaCl. The dissolved protein was applied to a 1.6×100 cm column of Ultrogel AcA54 (acrylamide agarose ultrogel having 5 to 70 k dalton fractionation) equilibrated in the same buffer. The CSF activity eluted from the column with an apparent molecular weight of about 19 k Daltons or after about 90 ml. It has been observed that if the gel filtration is performed at low ionic strength, CSF activity is eluted from the column in two positions with apparent molecular weights of about 19 k Daltons and about 38 k Daltons, suggesting that GM-CSF may readily form dimers.) The active fractions were pooled and brought to 0.15% TFA (by addition of 10% (v/v) TFA) and applied to a Vydac C4 column (0.46×25 cm) equilibrated in 0.1% TFA. The column was developed with a linear gradient of 0–90% (v/v) acetonitrile (1 ml/min., 340 ml total) in 0.1% TFA. The CSF activity eluted between 39 and 43% acetonitrile (Fractions 16–20). A 20 ul sample of Fraction 19 was analyzed by SDS polyacrylamide gel electrophoresis (13.5% gel as described by Lammli, op. cit). A single broad protein band with an apparent range of 18 to 26 k Daltons was observed, again consistent with the extensive glycosylate of the CSF protein (FIG. 2). Protein from Fraction 19 was submitted to Edman Degradation using the Applied Biosystems gas phase microsequenator. From approximately 20 ug of protein applied, the sequence of the first 16 amino acids was obtained (A-P-A-R-S-P-S-P-S-T-Q-P-W-E-H-V). The high yield of this single sequence strongly suggest that the CSF protein in Fraction 19 had been purified to homogeneity.

Bioassay indicated that the Fraction 19 CSF had $3\times10^7$ units per $A_{280}$ absorbance unit in the bone marrow assay. Since typical proteins in aqueous solution exhibit a range of extinction coefficients of 0.8 to 1.2 $A_{280}$ absorbance units per milligram, the specific activity of the purified CSF is between about $1\times10^7$ and about $4\times10^7$ units/mg when assayed using the human bone marrow cell assay.

This invention has been described in detail, including the preferred embodiments thereof. However, it will be appreciated that those skilled in the art, upon consideration of this specification, may make modifications and improvements within the spirit and scope of the invention.

For instance, it has been shown that murine CSFs activate neutrophils. Thus, it would be expected that the primate CSFs of the present invention will also activate neutrophils. Therefore, physiological functions of CSF may be severalfold. In the bone marrow, this lymphokine can stimulate proliferation and differentiation of effector cells for host defense while, in the periphery, new and existing cells can be activated. In a localized immunological response CSF can retain circulating neutrophils in or away from areas of inflammation. Inappropriate localization and/or activation of neutrophils can be involved in the pathophysiology of a variety of immune-mediated disorders such as rheumatoid arthritis.

What is claimed is:

1. A composition comprising purified and isolated native granulocyte macrophage-colony stimulating factor (GM-CSF) protein and a diluent, said purified and isolated GM-CSF protein having a sequence of 127 amino acids, the N-terminal sequence being Ala-Pro-Ala-Arg-Ser-Pro-Ser-Pro-Ser-Thr-Gln-Pro-Trp-Glu-His-Val and a specific activity in the human bone marrow assay of at least about $1\times10^7$ units per milligram of protein, wherein the GM-CSF protein has a molecular weight of about 15,000 to about 26,000 Daltons by SDS-PAGE.

2. The GM-CSF protein of claim 1 having a specific activity in the human bone marrow assay of at least about $4\times10^7$ units per milligram as determined by absorbance at 280 nanometers.

3. The GM-CSF protein composition of claim 1 which is human origin GM-CSF.

4. A pharmaceutical composition for the treatment of myelo-suppression in primates comprising the GM-CSF protein composition of claim 1, wherein said diluent is a pharmaceutically acceptable carrier.

5. The GM-CSF protein composition of claim 1 which shows size heterogeneity due to glycosylation when fractionated by SDS-PAGE.

6. The GM-CSF protein composition of claim 5 which is human origin GM-CSF.

7. The GM-CSF protein composition of claim 6 which appears as a single broad band on SDS-PAGE under denatured and reduced conditions corresponding to a molecular weight range of 18,000 to 26,000 Daltons.

8. The GM-CSF protein composition of claim 6 which has a molecular weight in the range of 28,000 to 30,000 Daltons as determined by SDS-PAGE.

9. The GM-CSF protein composition of claim 6 in which said 127 amino acid residues are sequentially the following 127 amino acid residues:

| Ala | Pro | Ala | Arg | Ser | Pro | Ser | Pro | Ser | Thr | Gln | Pro | Trp | Glu | His |
|---|---|---|---|---|---|---|---|---|---|---|---|---|---|---|
| Val | Asn | Ala | Ile | Gln | Glu | Ala | Arg | Arg | Leu | Leu | Asn | Leu | Ser | Arg |
| Asp | Thr | Ala | Ala | Glu | MET | Asn | Glu | Thr | Val | Glu | Val | Ile | Ser | Glu |
| MET | Phe | Asp | Leu | Gln | Glu | Pro | Thr | Cys | Leu | Gln | Thr | Arg | Leu | Glu |
| Leu | Tyr | Lys | Gln | Gly | Leu | Arg | Gly | Ser | Leu | Thr | Lys | Leu | Lys | Gly |
| Pro | Leu | Thr | MET | MET | Ala | Ser | His | Tyr | Lys | Gln | His | Cys | Pro | Pro |
| Thr | Pro | Glu | Thr | Ser | Cys | Ala | Thr | Gln | Thr | Ile | Thr | Phe | Glu | Ser |
| Phe | Lys | Glu | Asn | Leu | Lys | Asp | Phe | Leu | Leu | Val | Ile | Pro | Phe | Asp |
| Cys | Trp | Glu | Pro | Val | Gln | Glu. | | | | | | | | |

10. A pharmaceutical composition for the treatment of myelo-suppression in primates comprising the GM-CSF protein composition of claim 6, wherein said diluent is a pharmaceutically acceptable carrier.

\* \* \* \* \*

UNITED STATES PATENT AND TRADEMARK OFFICE
CERTIFICATE OF CORRECTION

PATENT NO. : 5,895,646
DATED : April 20, 1999
INVENTOR(S) : ELIZABETH A. WANG

It is certified that error appears in the above-identified patent and that said Letters Patent is hereby corrected as shown below:

ON THE TITLE PAGE [73]

Assignee, "Basel, should read --Basle,--.

REFERENCES CITED [56]

Other Publications,
"Yunis, et al., FEBS Letters, 1978, 90: 279-82.
Wu, et al. J. Biol. Chem., 1979, 254: 6226-28.
Gasson, et al. Science, 1984, 226: 1339-1342.
Fojo, et al., Biochemistry, 1978, 17: 3109-16.
Lusis, et al., Blood, 1981, 57: 13-21."
should be deleted; and
"Fojo, et al., Biophys. Acts., 1977, 494: 92-99.
Price, et al., Biochem. J., 1975, 148: 209-17."
should be deleted.

In "Miller et al;" "Colony-Fomring" should read
--Colony-Forming--;
In "Wu, . . . etc." "TLymphocyte" should read
--T-Lymphocyte--;
In "Price et al., . . . etc." "fro" should read
--from--;
In "Gasson et al;" "Purification" should read
--Purified--;
In "Fojo et al.," "Chaaracterization" should read
--Characterization--; and
In "Lusis et al., Blood 57, 13-21 (1981)." (second
occurrence) should be deleted.

UNITED STATES PATENT AND TRADEMARK OFFICE
CERTIFICATE OF CORRECTION

PATENT NO.    :   5,895,646
DATED         :   April 20, 1999
INVENTOR(S)   :   ELIZABETH A. WANG It is certified that error appears in the above-identified patent and that said Letters Patent is hereby corrected as shown below:

COLUMN 3

Line 45, "above mentioned" should read --above-mentioned--.

COLUMN 5

Line 39, "medium+10%" should read --medium + 10%--.

COLUMN 6

Line 56, "DME+10%" should read --DME + 10%--.

COLUMN 7

Line 17, "then" should read --and then--.

Signed and Sealed this

First Day of February, 2000

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,895,646

DATED : April 20, 1999

INVENTOR(S) : Elizabeth A. Wang

It is certified that error appears in the above-identified patent and that said Letters Patent is hereby corrected as shown below:

ON THE TITLE PAGE

[73] Assignee, "Novartis Corporation" should read --Novartis A.G.--.

Signed and Sealed this

Eighteenth Day of July, 2000

Attest:

Q. TODD DICKINSON

*Attesting Officer*   *Director of Patents and Trademarks*